(12) United States Patent
Geistlich et al.

(10) Patent No.: US 8,992,946 B2
(45) Date of Patent: Mar. 31, 2015

(54) METHOD AND MEMBRANE FOR TISSUE REGENERATION

(75) Inventors: Peter Geistlich, Stansstad (CH); Lothar Schloesser, Darmstadt (DE)

(73) Assignee: Geistlich Pharma AG, Wolhusen (CH)

(*) Notice: Subject to any disclaimer, the term of this patent is extended or adjusted under 35 U.S.C. 154(b) by 223 days.

(21) Appl. No.: 13/144,428

(22) PCT Filed: Jan. 18, 2010

(86) PCT No.: PCT/IB2010/000200
§ 371 (c)(1),
(2), (4) Date: Jul. 13, 2011

(87) PCT Pub. No.: WO2010/082138
PCT Pub. Date: Jul. 22, 2010

(65) Prior Publication Data
US 2011/0274756 A1    Nov. 10, 2011

Related U.S. Application Data

(60) Provisional application No. 61/145,334, filed on Jan. 16, 2009.

(51) Int. Cl.
*A61K 9/00*    (2006.01)
*A61L 31/04*   (2006.01)
*A61L 31/14*   (2006.01)

(52) U.S. Cl.
CPC .............. *A61L 31/044* (2013.01); *A61L 31/146* (2013.01); *A61L 31/148* (2013.01)
USPC ........................................................ 424/400

(58) Field of Classification Search
CPC ............................. A61L 31/044; A61L 31/148
See application file for complete search history.

(56) References Cited

U.S. PATENT DOCUMENTS

| | | |
|---|---|---|
| 5,766,631 A | 6/1998 | Arnold |
| 2002/0160036 A1 | 10/2002 | Geistlich et al. |
| 2007/0031388 A1 * | 2/2007 | Geistlich ...................... 424/93.7 |

(Continued)

FOREIGN PATENT DOCUMENTS

| | | | |
|---|---|---|---|
| EP | 1252903 A1 * | 10/2002 | .............. A61L 27/24 |
| JP | 07-204261 A | 8/1995 | |

(Continued)

OTHER PUBLICATIONS

Vardaxis et al, Confocal laser scanning microscopy of porcine skin: implications for human wound healing studies, J. Anat., 1997, vol. 190, pp. 601-611.*

(Continued)

*Primary Examiner* — Paul Dickinson
(74) *Attorney, Agent, or Firm* — Rothwell, Figg, Ernst & Manbeck, P.C.

(57) ABSTRACT

Tissue regeneration or grafting is promoted utilizing a structure including a multi-layer sheet of collagen membrane material which includes a purified collagen barrier sheet material derived from natural collagen-containing tissue, the barrier sheet material including a barrier layer with an outer smooth barrier face and a fibrous face opposite the smooth barrier face. The structure further includes a matrix layer of collagen sponge material adjacent to the fibrous face. The matrix layer of collagen sponge material is resorbed by a body of a subject at a substantially faster rate than the barrier sheet material.

19 Claims, 1 Drawing Sheet

(56) References Cited

U.S. PATENT DOCUMENTS

| | | |
|---|---|---|
| 2007/0038299 A1 | 2/2007 | Stone et al. |
| 2008/0107710 A1 | 5/2008 | Geistlich et al. |
| 2009/0148486 A1* | 6/2009 | Lu et al. .................. 424/422 |

FOREIGN PATENT DOCUMENTS

| | | |
|---|---|---|
| JP | 9-507144 A | 7/1997 |
| JP | 2000-507847 A | 6/2000 |
| JP | 2001-519210 A | 10/2001 |
| JP | 2003-010313 A | 1/2003 |
| WO | 2007/028078 A2 | 3/2007 |
| WO | 2008/067085 A2 | 6/2008 |

OTHER PUBLICATIONS

Jin Qiming et al.: "Nanofibrous Scaffolds Incoporating PDGF-BB Microspheres Induce Chemokine Expression and Tissue Neogenesis In Vivo," PLOS ONE, vol. 3, No. 3, Mar. 5, 2008, pp. 1-9.

* cited by examiner

METHOD AND MEMBRANE FOR TISSUE REGENERATION

CROSS REFERENCE TO RELATED APPLICATIONS

This application is a 35 U.S.C. 371 National Phase Entry Application from PCT/IB2010/000200, filed Jan. 18, 2010, and designating the United States, which claims benefit of U.S. provisional application No. 61/145,334 filed on Jan. 16, 2009, all of which is incorporated herein by reference in its entirety for all purposes.

BACKGROUND OF THE INVENTION

1. Field of the Invention

The present invention relates generally to methods for regeneration, repair or grafting of tissue.

2. Discussion of the Background Art

Various membrane types have been used in the repair and regeneration of a number of tissue types, including skin, mucosa, meniscus, cartilage, vertebral discs, ligament and bone.

Skin grafting for repair of damaged skin tissue has been an established procedure for some time. The use of split thickness skin grafts and oral mucosal free grafts in vestibular deepening and other types of related surgery in the oral cavity has also been an established procedure for some time. In addition, the use of free mucosal grafts taken from the palate and from the buccal mucosa has been used in re-establishing attached mucosal surfaces in edentulous alveolar ridge areas particularly in conjunction with the use of root form implants.

While such grafting procedures are well established, the development of an effective alloplastic or xenogeneic substitute graft material for the reconstruction and regeneration of normal skin and mucous membrane would bring about a much wider application of vestibuloplasty or other surgical procedures.

U.S. Pat. No. 6,713,085 discloses a membrane for skin and mucosa regeneration comprising a barrier layer including an outer smooth collagen barrier face and an opposite fibrous face, to which a matrix layer of collagen which may be applied to the fibrous collagen face as a slurry.

There remains a need in the art for improvements in promoting regeneration of tissue, e.g., following surgical procedures.

SUMMARY OF THE INVENTION

In accordance with the present invention, tissue regeneration, repair or grafting may be promoted utilizing a resorbable multi-layer structure which includes a purified collagen barrier sheet material derived from natural collagen-containing tissue and an additional collagen sponge layer. The barrier sheet material comprises a barrier layer including an outer smooth barrier face, and a fibrous face opposite said smooth barrier face. The multi-layer structure further comprises a matrix layer of collagen sponge material adjacent to the fibrous face. The matrix layer of collagen sponge material is resorbed by the body at a faster rate than the collagen sheet material.

DETAILED DESCRIPTION OF THE PREFERRED EMBODIMENTS

Figure 1:
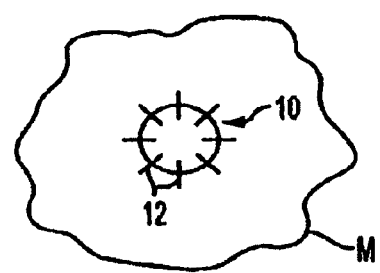
FIG. 1 is a plan view showing a patch of collagen material covering an area of tissue to be treated according to the present invention.

In accordance with certain embodiments, the present invention provides a composition and method for promoting regeneration or repair of tissue such as mucosa (oral, urogenital), skin, meniscus, cartilage, vertebral disc, bone and ligament.

In certain embodiments, the invention provides a composition and method for promoting regeneration or repair of mucosa. In connection with the treatment of mucosa, while the method sometimes is described in connection with promoting regeneration or repair of mucosa in the oral cavity following specific types of oral surgery, it will be appreciated that the method can be employed to promote regeneration or repair of mucosa in any part of the body having damaged mucosal tissue.

While the invention sometimes is described with respect to repair and regeneration of mucosa tissue in the treatment of mucosa injury, it is to be understood that the invention also is applicable to regeneration and repair of other tissue types, such as skin, meniscus, cartilage, vertebral disc, ligament and bone.

In certain embodiments, the invention provides a composition and method for promoting regeneration of damaged, injured, diseased, wounded, removed or missing tissue and promoting or facilitating a tissue graft on a body of a subject.

In certain embodiments, a method for promoting tissue regeneration, for promoting tissue repair, for promoting or facilitating a tissue graft, or a combination thereof, comprises covering an area of damaged, injured, diseased, wounded, removed or missing tissue of a body of a subject, with a tissue regeneration- or graft-promoting resorbable multi-layer structure which includes a purified collagen barrier sheet material derived from natural collagen-containing tissue, wherein said collagen barrier sheet material comprises a barrier layer including an outer smooth barrier face and further including a fibrous face opposite said smooth barrier face, wherein said multi-layer structure further comprises a matrix layer comprising collagen sponge material. The method further comprises at least one of adapting, adhering and fixing the collagen barrier sheet material over said area, with said matrix layer positioned between said area and said fibrous face, and allowing said area to heal or regenerate tissue, wherein said matrix layer of collagen sponge material is resorbed by the body of the subject at a substantially faster rate than said collagen barrier sheet material.

The patch may be fixed over an area of the tissue to be treated, e.g., with sutures or fibrin glue, and the tissue is allowed to heal or regenerate.

In certain embodiments, the said multi-layer structure has a thickness of about 0.5-8 mm.

In certain embodiments, the collagen sponge matrix layer comprises porcine collagen S, bovine collagen I/III, recombinant collagen I or III, recombinant collagen I/III or a mixture thereof. In certain embodiments, the collagen sponge matrix layer also comprises chitosan, elastin or hyaluronic acid, usually in a proportion of 0 to 30% by weight.

In certain embodiments, a method of the invention includes the steps of covering an area of damaged, injured, diseased, wounded, removed or missing tissue of a body of a subject, with a collagen sponge matrix material. The collagen sponge material is then covered by a purified collagen sheet material derived from natural collagen-containing tissue, wherein the sheet material comprises a barrier layer including an outer smooth barrier face, and further including a fibrous face opposite said smooth barrier face. The sponge material is adjacent to the fibrous face of the purified collagen sheet material, wherein the matrix layer is between the area to be treated and fibrous face.

In certain embodiments, the invention is a tissue regeneration/repair- or graft-promoting structure for promoting tissue regeneration, or for promoting or facilitating a tissue graft, by covering an area of damaged, injured, diseased, wounded, removed or missing tissue of a body of a subject, comprising a resorbable multi-layer structure which includes a purified collagen barrier sheet material derived from natural collagen-containing tissue, wherein the barrier sheet material comprises a barrier layer including an outer smooth barrier face and further includes a fibrous face opposite said smooth barrier face, wherein said multi-layer structure further comprises a matrix layer comprising collagen sponge material adjacent to said fibrous face, wherein said matrix layer of collagen sponge material is adapted to be positioned adjacent said area, and said multi-layer structure is adapted so that said matrix layer is resorbed by a body of a subject at a substantially faster rate than said collagen barrier sheet material.

In certain embodiments, the matrix layer is adhered or attached to said fibrous face. In certain embodiments, the multi-layer structure has a thickness of about 0.5-8 mm. In certain embodiments, the collagen sponge matrix layer comprises collagen of animal or human as well as recombinant source such as porcine collagen S, bovine collagen I/III, recombinant collagen I or III, recombinant collagen I/III or a mixture thereof. In certain embodiments, the collagen sponge matrix layer also comprises chitosan, elastin or hyaluronic acid, usually in a proportion of 0 to 30% by weight. In certain embodiments, the multi-layer structure carries at least one growth factor. In certain embodiments, the at least one growth factor is selected from the group consisting of Epidermal Growth Factor (EGF), Insulin-like Growth Factor (IGF-1), a member of Fibroblast Growth Factor family (FGF), Keratinocyte Growth Factor (KGF), Platelet-derived Growth Factor (PDGF), Transforming Growth Factor (TGF-β), CIF (Cartilage Inducing Factor), at least one of BMPs 1-14 (Bone Morphogenic Proteins), Granulocyte-macrophage colony-stimulating factor (GM-CSF), or a mixture thereof. In certain embodiments, the growth factor is PDGF.

In certain embodiments, the matrix layer is adapted to be resorbed by a body of a subject at about a same rate as growth of tissue cells, notably cells of mesenchymal and ectodermal origin underlying said membrane matrix layer in said area. This rate being modified in case of inclusion of growth factor(s). In certain embodiments, the said matrix layer is adapted to be resorbed by a body of a subject at about a same rate as growth of tissue cells neighbouring said membrane matrix layer in said area, wherein said cells are epithelial cells. This rate being modified in case of inclusion of growth factor(s). In certain embodiments, the matrix layer is adapted to be substantially completely resorbed by said body within about 2-5 weeks after said covering. In certain embodiments, the collagen barrier sheet material is adapted to be substantially completely resorbed within about 6-11 weeks after said covering. In certain embodiments, the structure is adapted so that said collagen barrier sheet material covers said area without complete resorption, at least about 50% longer than substantially complete resorption of the matrix sponge layer by the body. In certain embodiments, the structure is adapted so that said collagen barrier sheet material covers said area, without complete resorption, at least about 100% longer than substantially complete resorption of the matrix sponge layer by the body.

In accordance with certain embodiments of the present invention, as shown in FIG. 1, a defect or area to be treated in a tissue of tissue surface M of a subject may be repaired by placing a patch 10 over the defect and securing the patch to margins of the tissue surface around the defect. The patched area may be then allowed to heal or regenerate tissue. In FIG. 1, the patch 10 is shown secured by sutures 12 to the tissue surface M. Alternatively, the patch can be secured over the defect by adhesively bonding the patch to the surrounding host tissue or other structures surrounding the area to be treated, for example, utilizing an organic glue (e.g., fibrin glue) as is known in the art, or any other suitable method.

The patch 10 may be formed of a structure comprising a collagen barrier sheet material with appropriate pliability to conform closely to the shape of the tissue surface against which it is placed. In one embodiment, the collagen barrier sheet material has sufficient strength to accommodate suturing to the tissue and to protect the tissue surface from trauma during the healing process.

Figure 2:
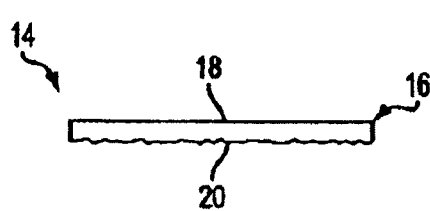
FIG. 2 is a sectional side view showing a collagen barrier sheet used in preparing the resorbable multi-layer structure of FIG. 3.

A collagen barrier sheet material for forming a patch in accordance with one embodiment of the present invention is shown in FIG. 2 at 14. The patch 14 includes a single collagen barrier layer 16 having a smooth barrier face 18 on one side and a textured or fibrous face 20 on the other side opposite the smooth face. The smooth face 18 may be non-porous to provide mechanical protection of the injured area. The fibrous face 20 allows cell growth thereon. In use, the smooth face may be oriented away from the area to be treated, and the fibrous face may be oriented toward the area to be treated.

In certain embodiments, the collagen barrier sheet material 16 may be predominantly collagen I, collagen III or a mixture thereof. One suitable material for this layer is BioGide®, from Ed. Geistlich Söhne AG für Chemische Industrie. The BioGide® material is derived from porcine peritoneal membrane, and is described in U.S. Pat. No. 5,837,278, incorporated herein by reference.

Figure 3:
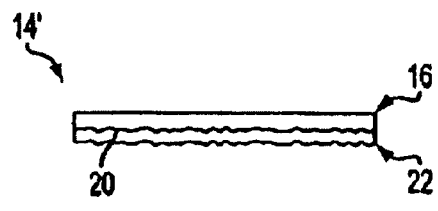
FIG. 3 is a sectional side view showing a resorbable multi-layer structure in accordance with the present invention.

FIG. 3 shows a multi-layer structure 14' that can be used in accordance with the present invention. This membrane includes a first collagen barrier layer 16 as shown in FIG. 2, and further includes a second collagen matrix layer 22, which may or may not be attached or adhered to the fibrous face 20 of the first collagen barrier sheet material layer 16 for placement against the tissue surface to promote regeneration or grafting of tissue. The collagen of the second matrix layer 22 may comprise or consist essentially of collagen sponge with substantial effects on cell adhesion, proliferation, invasion and differentiation properties for regeneration/repair cells.

In certain embodiments, both the collagen barrier sheet material layer and collagen sponge matrix layer are completely resorbable by the body of a subject.

In certain embodiments, the matrix layer is resorbed by the body of said subject at about a same rate as growth of tissue cells underlying said membrane matrix layer in said area. This rate being modified in case of inclusion of growth factor(s). In certain embodiments said cells are epithelial cells, endothelial cells, chondrocytes, synovial cells, spinal disc cells, tenocytes, or osteoblasts. In certain embodiments, the cells are epithelial cells. In certain embodiments, the matrix layer is substantially completely resorbed by said body within about 2-5 weeks after said covering. In certain embodiments, the collagen barrier sheet material is substantially completely resorbed within about 6-11 weeks after said covering. In certain embodiments, at least a portion of said collagen barrier sheet material covers said area, without complete resorption, at least about 50% longer than substantially complete resorption of said matrix layer by said body. In certain embodiments, the at least a portion of said collagen barrier sheet material covers said area, without complete resorption, at least about 100% longer than substantially complete resorption of said matrix layer by said body.

Collagen sponge (e.g., a product of Geistlich Pharma AG, Wolhusen, Switzerland), may be formed from connective tissue of various animal and organ source such as calf or porcine skin tissue. In certain embodiments, the collagen sponge may be predominately collagen I, e.g., greater than 50% collagen I, e.g., about 95% collagen I. The collagen sponge also may contain collagen III, e.g., in an amount of about 5% by weight. In certain embodiments, the collagen sponge matrix layer also comprises chitosan, elastin or hyaluronic acid, usually in a proportion of 0 to 30% by weight. The collagen sponge may be resorbed by the body of a subject at about the same rate as growth of tissue cells (such as epithelial cells) underlying the inventive structure in the area being treated. The collagen sponge matrix layer may be comprised of a fibrous structure which supports new tissue formation via substantial effects on cell adhesion, proliferation, invasion and differentiation. In certain embodiments, the collagen sponge matrix layer may be applied as a slurry and adhered to the fibrous layer opposite the barrier layer through drying, e.g., by freeze-drying.

In certain embodiments, the barrier layer remains in the body at least about 50% longer than the sponge layer, prior to complete resorbtion. In other embodiments, the barrier layer remains in the body at least about 75%, 100%, 125%, 150%, 175% or at least about 200% longer than the sponge layer prior to complete resorbtion.

The barrier layer of the structure may cover the area being treated for at least about 6-11 weeks or longer, e.g., about at least 6-8 weeks, prior to complete resorption of the barrier layer.

In certain embodiments, the collagen sponge matrix layer may be completely resorbed within at least about 2-5 weeks or longer, with the barrier sheet remaining for at least about an additional 5-6 more weeks or longer, after substantially complete resorption of the collagen sponge matrix layer.

In certain embodiments, the time of resorption of the collagen patch construct may be altered by treating the composed patch material with UV radiation, dehydrothermal treatment (100-160° C., vacuum, 12-240 h), zerolength or non-zerolength crosslinkers for chemical crosslinking e.g. with a carbodimide such as EDC ((N-Ethyl-N'-(3-dimethylaminopropyl)-carbodiimide-hydrochloride, CDI (N,N-Carboxydiimidazole), CMC (1-cyclohexyl-3-(2-morpholinoethyl)carbodiimide), aldehydes/dialdehydes (formaldehyde, glutaraldehyde, hyaluronic acid aldehyde), crosslinkers from plant origin (e.g. genipin) and aldoses/ketoses (e.g. ribose) or the like, or combinations thereof.

A BioGide® barrier material as described above typically has a resorption rate in the body of about 6-8 weeks. The time of resorption of both the barrier and the collagen sponge layer can be controlled by cross-linking. For example, the collagen sponge layer can be cross-linked so as to achieve complete resorption within about 2-5 weeks in a body by application of UV radiation by a UV lamp of about 10-20 W (e.g., about 15 W), at about 15-45 cm (e.g., about 30 cm) distance from the collagen sponge layer surface of the double layer membrane for about 2-4 hours (e.g., about 3 hours). An exemplary wavelength is UV-C rays within about 100 nm to about 280 nm (e.g., 253.7 nm). In another example, cross-linking by dehydrothermal treatment may take place under vacuum at <200 mbar and 100 degrees Celsius for 24 hours. Cross-linking with EDC may be done with an aqueous solution of about 0.1-0.6 g EDC per about 0.3-2 g collagen sponge matrix (e.g., about 0.3 g EDC per 1.0 g collagen matrix). Other cross-linking agents such as hyaluronan, hexethylendiisocyamate, N-hydroxysuccinimide (NHS) and gloxal may be used. Per gram of collagen, about 10 to 300 mg (e.g., about 100 mg) hyaluronic acid aldehyde may be used for cross-linking.

In certain embodiments, included in the collagen sponge slurry is heparin, heparin derived oligosaccharides, hyaluronic acid, glycosaminoglycans, (e.g. chondroitin-4-sulphate) or a mixture thereof (1-30% by weight, e.g., 2-10% by weight).

In addition, the combination of the first and second layers 16 and 22 increases the thickness of the membrane 14' for easy handling and improved healing. The thickness of the membrane can vary depending upon application but will typically range from about 0.5 mm to about 8 mm, with a possible range between about 2 mm and about 5 mm, and a thickness of about 3 mm being one possibility.

The first layer 16 in the embodiments shown in FIGS. 2 and 3 can be produced in a variety of ways including, but not limited to, the process steps described in U.S. Pat. No. 5,837,278; by using other animal tissues (pleura, mesenterium, pericard, dura, intestine) and/or membranes, by de-airing and air-drying a slurry (film-like transparent membrane); by de-airing and vacuum-drying a slurry (film-like transparent membrane); or using compressed sponges. The first layer 16 can be made of collagen I, II, III, IV, IX, X and XI of porcine, bovine, horse or recombinant technology of origin or combinations of these collagen types.

The second collagen sponge matrix layer 22 in one embodiment as shown in FIG. 3 is e.g., a freeze-dried collagen slurry.

The second collagen sponge layer 22 may be formed from bovine, porcine or recombinant skin material, and may be formed from porcine skin material, bovine collagen I/III, or recombinant collagen I and recombinant collagen I/III and may further comprise chitosan, elastin or hyaluronic acid, usually in a proportion of 0 to 30% by weight.

In the embodiment shown in FIG. 3, the first and second membrane layers 16 and 22 can be connected to one another, or combined, in any suitable manner. Examples of three suitable methods of combination include: attaching the first membrane layer to the second membrane layer with fibrin glue or any other type of glue; attaching the first membrane layer to the second membrane layer using collagen slurry; or coating the first membrane layer with a collagen sponge slurry, and then freeze-drying the combination.

It is possible to use the combined first and second layers without any further materials like growth factors.

In certain embodiments, at least one growth factor such as EGF (Epidermal Growth Factor), IGF-1 (Insulin-like Growth Factor), a member of Fibroblast Growth Factor family (FGF), Keratinocyte Growth Factor (KGF), PDGF (Platelet-derived Growth Factor AA, AB, BB), TGF-β (Transforming Growth Factor family-β1, β2, β3), CIF (Cartilage Inducing Factor), at least one of BMP's 1-14 (Bone Morphogenic Proteins), Granulocyte-macrophage colony-stimulating factor (GM-CSF), or mixtures thereof, which may promote tissue regeneration, can be charged to or within the inventive structure, and/or added to the surface of the membrane that may be placed against the tissue to be treated. In certain embodiments, the growth factor is PDGF.

It is possible to deliver pharmacological and/or biological active substances e.g., growth factors, in a release system, e.g., a time-release form, such as microspheres, gelatine beads, and the like. Such forms can be charged to the inventive structure, e.g., embedded or encapsulated therein.

The invention further relates to use of a structure as defined herein, or components thereof, for tissue regeneration or grafting, and to use of a structure as defined herein, or components thereof, in manufacture of a pharmaceutical preparation for promoting tissue regeneration or grafting.

In certain embodiments, a multi-layer patch according to the invention may be prepared as follows:

(A) The first membrane layer may be produced in accordance with the procedure described in U.S. Pat. No. 5,837,278, having a barrier surface and a fibrous surface (e.g., Bio Gide® membrane from Geistlich Pharma AG, Wolhusen, Switzerland).

(B) Collagen sponge may be obtained from Geistlich Pharma AG, Wolhusen, Switzerland, and formed into a slurry. The slurry may be applied as a substantially homogenous layer to the fibrous surface of the first membrane, which optionally contains chitosan, elastin or hyaluronic acid, and dried, preferably freeze-dried, to produce a multi-layered structure in accordance with the present invention.

NON-LIMITING EXAMPLES

Example 1

Patch with Collagen Sponge Part

1. Soaking of a pure collagen sponge (from porcine skin, 95% collagen I, 5% collagen III) with water (30 minutes, constantly stirring)
2. First dispersing of the soaked collagen with a colloid mill in the same water (100 kg collagen slurry, 2%)
3. Regulating the pH value to 3.3 with hydrochloric acid.
4. Second dispersing of the collagen slurry with a colloid mill
5. Readjusting the pH to 3.3 with hydrochloric acid
6. Filling the slurry in the freeze drying trays to a fill up quantity of 5 mm
7. Applying the collagen slurry to the fibrous side of Bio Gide® collagen membranes
8. freeze drying

Example 2

Patch with Collagen/Elastin Sponge Part

1 Soaking of a pure collagen sponge (from porcine skin, 95% collagen I, 5% collagen III) with water (30 minutes, constantly stirring)
2 First dispersing of the soaked collagen with a colloid mill in the same water (100 kg collagen slurry, 2%)
3 Regulating the pH value to 3.3 with hydrochloric acid.
4 Adding the elastin suspension
   Preparation of the suspension:
   a. Passing elastin (lyophilized, Sigma) through a 4-000 mesh sieve to obtain elastin particle smaller 40 μm
   b. Swelling of the elastin over 24 h at 10-15° C. in water pH 3.3 with hydrochloric acid
   c. Suspending of the elastin in a blender to a homogenious suspension (10 kg elastin suspension 5%)
5 Second dispersing of the collagen/elastin slurry with a colloid mill
6 Readjusting the pH to 3.3 with hydrochloric acid
7 Filling the slurry in the freeze drying trays to a fill up quantity of 5 mm
8 Applying the collagen/elastin slurry to the fibrous side of Bio Gide® collagen membranes
9 freeze drying (sponge part of the final combination product: 20% elastin, 80% collagen)

Example 3

Patch with Collagen/Chitosan Sponge Part

1. Soaking of a pure collagen sponge (from porcine skin, 95% collagen I, 5% collagen III) with water (30 minutes, constantly stirring)
2. First dispersing of the soaked collagen with a colloid mill in the same water
   (100 kg collagen slurry, 2%)
3. Regulating the pH value to 3.3 with hydrochloric acid.
4. Adding the chitosan solution
   Preparation of the solution
   a. Chitosan was dispersed in deionized water
   b. Adding of 8% acetic acid
   c. Dissolving the chitosan by agitating for 1 hour at room temperature (10 kg solution, acetic acid 4%, chitosan 2.5%)
5. Second dispersing of the collagen/chitosan slurry
6. Readjusting the pH to 3.3
7. Filling the slurry in the freeze drying trays to a fill up quantity of 5 mm
8. Applying the collagen/chitosan slurry to the fibrous side of Bio Gide® collagen membranes
9. freeze drying (sponge part of the final combination product: 11% chitosan, 89% collagen)

Example 4

Patch with Collagen/Hyaluronic Acid Sponge Part

1. Soaking of a pure collagen sponge (from porcine skin, 95% collagen I, 5% collagen III) with water (30 minutes, constantly stirring)
2. First dispersing of the soaked collagen with a colloid mill in the same water to a 2% collagen slurry
3. Regulating the pH value to 3.3 with hydrochloric acid.
4. Adding the hyaluronic acid gel
   Preparation of the gel
   a. Dissolving sodium hyaluronate (molecular weight: $2 \times 10^6$ Da) in deionized water
   b. Adjusting to pH 3.3 with 1N hydrochloric acid (20 kg gel, hyaluronic acid 1%)
5. Second dispersing of the collagen/hyaluronic acid slurry
6. Readjusting the pH to 3.3 with hydrochloric acid
7. Filling the slurry in the freeze drying trays to a fill up quantity of 5 mm
8. Applying the collagen/hyaluronic acid slurry to the fibrous side of Bio Gide® collagen membranes
9. freeze drying (sponge part of the final combination product: 9% hyaluronic acid, 91% collagen)

Example 5

A human subject who had had skin bitten from his ear by a dog was treated using the inventive structure according to the invention. The membrane was stitched over the wound with sutures and the wound was allowed to heal. Surprisingly new skin was formed at the wound site, including hair follicles.

Since many modifications, variations and changes in detail may be made to the described embodiments, it is intended that all matter in the foregoing description and shown in the accompanying drawings be interpreted as illustrative and not in a limiting sense.

The invention claimed is:

1. A tissue regeneration- or graft-promoting structure for promoting tissue regeneration, for promoting tissue repair, or for promoting or facilitating a tissue graft or a combination thereof, by covering an area of damaged, injured, diseased, wounded, removed or missing tissue of a body of a subject, comprising a resorbable multi-layer structure which includes a purified collagen barrier sheet material derived from natural collagen-containing tissue, wherein the barrier sheet material comprises a barrier layer including an outer smooth barrier face and further includes a fibrous face opposite said smooth barrier face, wherein said multi-layer structure further comprises a matrix layer comprising collagen sponge material adjacent to said fibrous face, wherein said matrix layer of collagen sponge material is adapted to be positioned adjacent said area, and said multi-layer structure is adapted by crosslinking so that said matrix layer is resorbed by the body of a subject within about 2-5 weeks after said covering and said collagen barrier sheet material is resorbed by the body of a subject within about 6-11 weeks after said covering, wherein said multi-layer structure is adapted by a method selected from application of UV radiation by a UV lamp of about 10-20 W at about 15-45 cm distance from the collagen sponge layer surface of the membrane for about 2-4 hours, cross-linking by dehydrothermal treatment under vacuum at <200 mbar and 100° Celsius for 24 hours, cross-linking with EDC in an aqueous solution of about 0.1-0.6 g EDC per about 0.3-2 g collagen sponge matrix, using cross-linking agents such as hyaluronan, hexethylendiisocyamate, N-hydroxysuccinimide (NHS) or gloxal, and wherein said matrix layer comprises collagen material consisting essentially of porcine collagen sponge from porcine skin.

2. The structure of claim 1 where said matrix layer is adhered or attached to said fibrous face.

3. The structure of claim 1 wherein said collagen barrier sheet material is derived from animal tissues (pleura, mesenterium, pericard, dura, intestine).

4. The structure of claim 3 wherein said barrier sheet material comprises porcine peritoneal membrane.

5. The structure of claim 1 wherein said multi-layer structure has a thickness of about 0.5-8 mm.

6. The structure of claim 1 wherein said collagen sponge matrix layer further comprises chitosan, elastin or hyaluronic acid.

7. The structure of claim 1, wherein the multi-layer structure carries at least one growth factor.

8. The structure of claim 7 wherein said at least one growth factor is selected from the group consisting of Epidermal Growth Factor (EGF), Insulin-like Growth Factor (IGF-1), a member of Fibroblast Growth Factor family (FGF), Keratinocyte Growth Factor (KGF), Platelet-derived Growth Factor (PDGF), Transforming Growth Factor (TGF-β), CIF (Cartilage Inducing Factor), at least one of BMPs 1-14 (Bone Morphogenic Proteins), Granulocyte-macrophage colony-stimulating factor (GM-CSF), or a mixture thereof.

9. The structure of claim 8 wherein said growth factor is PDGF.

10. The structure of claim 2 wherein said collagen sponge material is adhered to said fibrous face by being applied to said fibrous face as a slurry, and then dried.

11. The structure of claim 10 wherein said collagen sponge matrix layer further comprises chitosan, elastin or hyaluronic acid.

12. The structure of claim 1 wherein said matrix layer is adapted to be resorbed by a body of a subject at about a same rate as growth of tissue cells underlying said membrane matrix layer in said area.

13. The structure of claim 12 wherein said matrix layer is adapted to be resorbed by a body of a subject at about a same rate as growth of tissue cells underlying said membrane matrix layer in said area, and wherein said cells are cells of mesenchymal or ectodermal origin.

14. The structure of claim 1, wherein said structure is adapted so that said collagen barrier sheet material covers said area without complete resorption, at least about 50% longer than substantially complete resorption of the matrix sponge layer by the body.

15. The structure of claim 1, wherein said structure is adapted so that said collagen barrier sheet material covers said area, without complete resorption, at least about 100% longer than substantially complete resorption of the matrix sponge layer by the body.

16. The structure of claim 7, wherein said growth factor is present in a time-release form.

17. The structure of claim 16, wherein said time-release form is comprised of microspheres.

18. A tissue regeneration- or graft-promoting structure for promoting tissue regeneration, for promoting tissue repair, or for promoting or facilitating a tissue graft or a combination thereof, by covering an area of damaged, injured, diseased, wounded, removed or missing tissue of a body of a subject, comprising a resorbable multi-layer structure which includes a purified collagen barrier sheet material derived from natural collagen-containing tissue, wherein the barrier sheet material comprises a barrier layer including an outer smooth barrier face and further includes a fibrous face opposite said smooth barrier face, wherein said multi-layer structure further comprises a matrix layer comprising collagen sponge material adjacent to said fibrous face, wherein said matrix layer of collagen sponge material is adapted to be positioned adjacent said area, and said multi-layer structure is adapted by crosslinking so that said matrix layer is resorbed by the body of a subject within about 2-5 weeks after said covering and said collagen barrier sheet material is resorbed by the body of a subject within about 6-11 weeks after said covering, wherein said multi-layer structure is adapted by a method selected from application of UV radiation by a UV lamp of about 10-20 W at about 15-45 cm distance from the collagen sponge layer surface of the membrane for about 2-4 hours, cross-linking by dehydrothermal treatment under vacuum at <200 mbar and 100° Celsius for 24 hours, cross-linking with EDC in an aqueous solution of about 0.1-0.6 g EDC per about 0.3-2 g collagen sponge matrix, using cross-linking agents such as hyaluronan, hexethylendiisocyamate, N-hydroxysuccinimide (NHS) or gloxal, and wherein said matrix layer comprises collagen sponge derived from porcine skin, bovine collagen I/III, recombinant collagen I or III, recombinant collagen I/III or a mixture thereof, and said matrix layer comprises chitosan or elastin.

19. The structure of claim 18, wherein said collagen sponge is derived from porcine skin.

* * * * *